(12) United States Patent
Kuhnau

(10) Patent No.: US 7,285,284 B2
(45) Date of Patent: Oct. 23, 2007

(54) COSMETIC COMPOSITION, METHOD OF USE AND METHOD OF MAKING

(76) Inventor: Stephen C. Kuhnau, 500 Ashlawn St., Harahan, LA (US) 70123

(*) Notice: Subject to any disclaimer, the term of this patent is extended or adjusted under 35 U.S.C. 154(b) by 0 days.

(21) Appl. No.: 10/102,721

(22) Filed: Mar. 22, 2002

(65) Prior Publication Data

US 2002/0142019 A1    Oct. 3, 2002

Related U.S. Application Data

(63) Continuation of application No. 09/658,119, filed on Sep. 8, 2000.

(51) Int. Cl.
*A61K 8/49* (2006.01)
*A61K 8/30* (2006.01)
*A61K 8/46* (2006.01)
*A61K 8/67* (2006.01)

(52) U.S. Cl. ............... 424/401; 424/776; 424/736; 424/489; 514/474; 514/184

(58) Field of Classification Search ............... 424/322, 424/401, 489, 776, 736; 514/474
See application file for complete search history.

(56) References Cited

U.S. PATENT DOCUMENTS

| 4,477,469 A | | 10/1984 | Herschler |
| 4,563,184 A | | 1/1986 | Korol |
| 5,360,824 A | * | 11/1994 | Barker .................. 424/680 |
| 5,431,913 A | * | 7/1995 | Phillips |
| 5,786,343 A | * | 7/1998 | Ber |
| 5,830,882 A | | 11/1998 | Falk et al. |
| 5,965,618 A | * | 10/1999 | Perricone .................. 514/558 |
| 6,162,419 A | | 12/2000 | Perricone et al. |
| 6,184,247 B1 | | 2/2001 | Schneider |

OTHER PUBLICATIONS

Idson, Treatment Cosmetics Overview—Part 3, (Nov. 1995), Drug & Cosmetic Industry, http://proquest.umi.com, printed Jun. 9, 2003.*
Siegel-Maier, Aug. 1999, What's Your Type? 20 Top Moisturizers for Your Skin, pp. 53-55.*
Alexander, P., Overwhelmed by a National Abundance, (1992), Manufacturing Chemist, vol. 63, No. 10, p. 43, pp. 43.

* cited by examiner

*Primary Examiner*—Sreeni Padmanabhan
*Assistant Examiner*—Gina C. Yu
(74) *Attorney, Agent, or Firm*—Arent Fox, LLP

(57) ABSTRACT

A cosmetic composition for use as scrubbing agent or a mask uses vitamin C particles or crystals in an oil base, whereby the particles are insoluble in the oil so that they remain as suspended scrubbing particles.

3 Claims, No Drawings

COSMETIC COMPOSITION, METHOD OF USE AND METHOD OF MAKING

This application is a continuation application of U.S. application Ser. No. 09/658,119, filed Sep. 8, 2000.

FIELD OF THE INVENTION

The present invention is directed to a cosmetic composition, a method of its use and a method of making the cosmetic composition. In particular, the present invention is related to a cosmetic composition containing vitamin C particles in an oil base for use as a scrubbing or mask agent.

BACKGROUND OF THE INVENTION

Various cosmetic compositions have been proposed in the prior art to function as skin cleansers or scrubbing agents. For example, U.S. Pat. No. 5,658,573 discloses a body care composition as a facial cleanser which contains colloidal silica particles in an aqueous suspension. Another example of a facial scrub is disclosed in U.S. Pat. No. 5,139,782, which discloses a cosmetic composition containing a high-silica zeolite, for removing retention products from a skin surface. While many cosmetic preparations or compositions include inorganic materials for cleansing purposes, a demand exists for all-organic compositions function as cleansers for skin scrubbing agents or masks.

Some cosmetic formulations uses organic agents such as walnut hulls, almond meal and corn meal.

Drawbacks with these prior art compositions include the use of water as the base material. Water has no therapeutic effect and its inclusion in these prior art compositions merely dilutes the active components.

Compositions containing scrubbing agents can be abrasive on the skin, causing redness or throbbing after use. Compositions containing food products such as walnut hulls require the addition of preservatives to prevent the food products from spoiling over time. The preservatives contribute to the cost of the product and further dilute the active components.

In view of the drawbacks noted above, a need exists for improved cosmetic scrubbing compositions. The present invention solves this need by providing an oil-based cosmetic composition containing insoluble vitamin C particles therein, for particular use as a skin scrubbing agent or mask.

Vitamin C has been used as an active ingredient for various kinds of cosmetics in view of its nutritive enriching effect, fair skin producing effect and the like. U.S. Pat. No. 4,818,521 discloses an emulsion cosmetic that contains, preferably between 1% and 10% by weight of the total weight of the cosmetic, vitamin C. U.S. Pat. No. 4,818,521 does not teach the use of vitamin C particles as an insoluble component of a cosmetic preparation or a composition whereby the particles function as a scrubbing or cleansing agent.

SUMMARY OF THE INVENTION

The first object of the present invention is to provide an improved cosmetic composition.

Another object of the invention is a method of using the improved cosmetic composition as a scrubbing agent for cleansing skin, wherein the improved cosmetic composition of the present invention is less abrasive than prior art agents.

A further object of the present invention is a method of using of the improved cosmetic composition as a facial mask.

The invention also includes a method of making the improved composition.

In one of the embodiments of the present invention, the cosmetic composition of the present invention comprises an effective amount of at least one form of vitamin C in an oil base. Optionally, the cosmetic composition of the present invention further comprises at least one organic sulfur compound. Examples of the organic sulfur compound include methyl sulfonyl methane (MSM), methyl sulfonyl ethane, ethyl sulfonyl ethane, methyl sulfonyl propane, ethyl sulfonyl propane and propyl sulfonyl propane. Preferably, the at least one organic sulfur compound is methyl sulfonyl methane.

Within the scope of the present invention is a cosmetic composition consisting essentially of an effective amount of at least one form of vitamin C and at least one organic sulfur compound in an oil base. The at least one organic sulfur compound is selected from the group consisting of methyl sulfonyl methane (MSM), methyl sulfonyl ethane, ethyl sulfonyl ethane, methyl sulfonyl propane, ethyl sulfonyl propane and propyl sulfonyl propane. Preferably, the at least one organic sulfur compound is methyl sulfonyl methane. The oil base preferably is a vegetable oil base, which can be sunflower oil, grapeseed oil, olive oil and the like. This embodiment of the cosmetic composition can contain additional ingredients selected from shea butter, vitamin E (D-α-tocopherol), cocoa butter, jojoba oil, green tea extract, alpha lipoic acid, grapefruit extract, and evening primrose oil.

The at least one form of vitamin C can be at least one oil insoluble form of vitamin C, at least one oil soluble form of vitamin C, or a mixture of at least one oil insoluble form of vitamin C and at least one oil soluble form of vitamin C.

The at least one oil insoluble form of vitamin C (i.e. at least one form of vitamin C insoluble in the oil base) can exist as vitamin C particles in the cosmetic composition, so that they function as a scrubbing agent when used on an individual's skin. Examples of the oil insoluble form of vitamin C include calcium ascorbate, magnesium ascorbate, zinc ascorbate, copper ascorbate, ferrous ascorbate, ferric ascorbate, sodium ascorbate, potassium ascorbate and nicotinamide ascorbate.

The at least one oil soluble form of vitamin C can provide nutritional value to the skin and help maintain the health of the skin by playing a role in collagen formation. Examples of the oil soluble form of vitamin C include ascorbyl laurate, ascorbyl myristate, ascorbyl palmitate, ascorbyl stearate, ascorbyl arachidate, ascorbyl palmitoleate, ascorbyl oleate, ascorbyl elaidate, ascorbyl linoleate, ascorbyl linolenate and ascorbyl arachindonate.

DETAILED DESCRIPTION OF THE INVENTION

The at least one oil insoluble form of vitamin C in the cosmetic composition of the present invention can amount to about 10 weight %-about 100 weight %, preferably about 30 weight %-about 80 weight %, more preferably about 40 weight %-about 70 weight % (e.g. about 44 weight %), of the total vitamin C present in the cosmetic composition. Most preferably, the amount of the at least one oil insoluble form of vitamin C is about 50 weight %-60 weight % of the amount of total vitamin C present in the cosmetic composition. Very good result can be obtained when the amount of the at least one oil insoluble form of vitamin C is about 57.4 weight % of amount of total vitamin C in the cosmetic composition of the present invention.

The effective amount of vitamin C is defined in terms of an amount which will not make the oil base too pasty so as to make the cosmetic composition too difficult to apply. Too much of the vitamin C particles will turn the cosmetic composition into a pasty or almost granular mix. However, an insufficient amount of particles will fail to generate enough surface particle area to perform the scrubbing or cleansing effect. The effective amount of the at least one oil soluble form of vitamin C is an amount of the oil soluble form of vitamin C that is effective in providing nutrition to the skin and maintaining the health of the skin by playing a role in collagen formation.

The total amount of vitamin C, i.e. oil insoluble forms, oil soluble forms, or mixtures of oil insoluble forms and oil soluble forms, in the cosmetic composition of the present invention can be about 2 weight %-about 90 weight % or about 5 weight %-about 80 weight % in terms of the total weight of the composition. Preferably, the cosmetic composition contains vitamin C in about 10 weight %-about 60 weight %. The amount of vitamin C in the cosmetic composition can be more preferably about 20 weight % to about 50 weight %, and even more preferably about 30 weight % to about 40 weight %. Very good results can be obtained when the cosmetic composition of the present invention contains 34 weight % total vitamin C.

As an insoluble particle, the vitamin C is preferably calcium ascorbate which is the calcium salt of L-ascorbic acid.

In one of the embodiments of the cosmetic composition of the present invention, the amount of the at least one oil insoluble form of vitamin C, e.g. calcium ascorbate, can be between about 2 weight % and about 80 weight %, preferably between about 8 weight % to about 50 weight %, more preferably between about 14 weight % to 35 weight %, and most preferably between about 17 weight % to about 25 weight %, of the total weight of the cosmetic composition. Good results can be obtained with 15 weight % or 19.5 weight % of the at least one oil insoluble form of vitamin C, e.g. calcium ascorbate, in terms of the total weight of the cosmetic composition.

The cosmetic composition of the present invention can contain the at least one oil soluble form of vitamin C, e.g. ascorbyl palmitate, in an amount of about 1 weight % to about 50 weight %, preferably about 5 weight % to about 40 weight %, more preferably about 10 weight % to 30 weight %, and most preferably about 14 weight % to about 20 weight %, of the total weight of the cosmetic composition. Good results can be obtained with 14.5 weight % or 19 weight % of the at least one oil soluble form of vitamin C in terms of the total weight of the cosmetic composition.

In the cosmetic compositions of the present invention, the amount of the at least one organic sulfur compound can be about 1 weight %-about 30 weight %, preferably about 2 weight %-about 15 weight %, more preferably about 4 weight %-about 10 weight %, of the total weight of the cosmetic composition of the present invention. Very good results can be obtained with a cosmetic composition containing 5 weight % of the organic sulfur compound, e.g. methyl sulfonyl methane, in terms of the total weight of the cosmetic composition.

The vitamin C particle-containing oil base cosmetic composition can be rubbed topically on a person's skin to function as a scrubbing or cleansing agent. Alternatively, the composition could also be used as a facial mask. In this mode, the composition would be applied for a period of time and then washed off. Exemplary time periods include one to several minutes.

The particles in the oil based composition provide a more gentle cleansing or scrubbing action due to their inherent characteristics than prior art scrubbing agents, particularly inorganic types. In other words, a smooth facial polish is obtained as a result of the similar size and shape of the particles. This contrasts with prior art formulations such as walnut hulls or almonds, both of which have irregular shapes and uneven size distributions.

The extra high concentration of vitamin C is also an advantage in terms of its high nutritive effect. In addition, since vitamin C is a natural preservative, there is no need to use other preservatives as part of the composition. Further, since the composition is not aqueous based, no water is present and the drawbacks associated therewith are overcome. The composition forms a rich emollient complex which softens the skin as well.

The present invention provides a cosmetic composition comprising the effective amount of at least one oil insoluble form of vitamin C particles in an oil base, optionally further comprising at least one oil soluble form of vitamin C and/or at least one organic sulfur compound selected from the group consisting of methyl sulfonyl methane (MSM), methyl sulfonyl ethane, ethyl sulfonyl ethane, methyl sulfonyl propane, ethyl sulfonyl propane and propyl sulfonyl propane.

In the cosmetic compositions of the present invention, the oil base is preferably a vegetable oil base such as sunflower oil, grapeseed oil, a combination thereof or the like. Other equivalent oils as would be known in the art could also be employed as the composition base. The base is non-aqueous so that the oil insoluble vitamin C crystals do not dissolve. The oil insoluble vitamin C crystals would dissolve in an aqueous base composition, thereby removing the composition's particles of crystals for scrubbing or cleansing purposes.

The inventive composition can also include vitamin C in its soluble form as ascorbyl palmitate. This form of vitamin C is soluble in the oil base and provides the inventive composition with the therapeutic effects of the vitamin C when in solution in the oil base.

A preferred form of the calcium ascorbate as vitamin C crystals is sold by Roche Vitamins and Minerals of Parsippany, N.J. or Solgar Laboratories of Leonia, N.J. Typically, these calcium ascorbate crystals comprise 97 parts of calcium ascorbate and three parts L-ascorbic acid. Using this material and an insoluble amount of about 13.0 wt. %, 12.61 wt. % would be calcium ascorbate and 0.39 wt. % would be L-ascorbic acid. Of course, other forms or mixtures of the insoluble vitamin C crystal for use as part of the invention can be used than the types obtainable by the two suppliers noted above.

The particle size of the crystals should be sufficiently fine so that a dispersion is obtained in the oil base. An exemplary particle size distribution is 100% passing through a 20 mesh, 96% passing through 40 mesh and 75% passing through 60 mesh.

Other components besides the oil insoluble forms of vitamin C, the oil soluble forms of vitamin C and the oil base can be added to the basic cosmetic composition. These include other oils such as grapeseed oil, olive oil and the like and shea butter, vitamin E (D-α-tocopherol), cocoa butter, jojoba oil, green tea extract, alpha lipoic acid, grapefruit extract, and evening primrose oil. The amounts of these additives can vary as would be known in the art. Exemplary ranges are listed in the Table below in terms of the weight of the cosmetic composition (the preferred ranges are listed in brackets).

TABLE 1

| INGREDIENTS | WEIGHT PERCENT |
| --- | --- |
| Sunflower Oil | about 5–50 (about 10–20) |
| Grapeseed Oil | about 10–20 (about 12–18) |
| Olive Oil | about 0.5–8.0 (about 1–4) |
| Shea Butter | about 2–35 (about 10–30) |
| Vitamin E | about 0.2–8.0 (about 1–4) |
| Cocoa Butter | about 1–10 (about 2–8) |
| Jojoba Oil | about 0.2–1 |
| Green Tea Extract | about .01–.06 |
| Alpha Lipoic | about 0.01–0.06 |
| Grapefruit Extract | about 0.01–0.06 |
| Evening Primrose Oil | about 0.2–1.2 |

The more preferred ranges of some of the ingredients in the oil base are sunflower oil, about 14-16 weight %; grapeseed oil, about 14-16 weight %; olive oil, about 1-2 weight %; shea butter, about 18-22 weight %; vitamin E, about 1-2 weight %; and cocoa butter, about 4.5-6 weight %, in terms of the total weight of the cosmetic composition, which can also contain 5 weight % of methyl sulfonyl methane, 19.5 weight % of a oil insoluble vitamin C, e.g. calcium ascorbate, and 14.5 weight % of a oil soluble vitamin C, e.g. ascorbyl palmitate.

The cosmetic composition of the invention can be produced in any form suitable for topical application on a skin. Exemplary forms include lotions, creams, oils and gels.

The present invention provides a method for making the cosmetic composition, comprising a step of mixing an effective amount of at least one form of vitamin C, the oil base, and at least one organic sulfur compound selected from the group consisting of methyl sulfonyl methane (MSM), methyl sulfonyl ethane, ethyl sulfonyl ethane, methyl sulfonyl propane, ethyl sulfonyl propane and propyl sulfonyl propane.

In an embodiment of the method for making the cosmetic composition, the at least one form of vitamin C can be at least a oil insoluble form of vitamin C, a oil soluble form of vitamin C, or a mixture of at least one oil insoluble form of vitamin C and at least one oil soluble form of vitamin C.

In another embodiment of the method for making the cosmetic composition, the at least one form of vitamin C is a mixture of at least one oil insoluble form of vitamin C and at least one oil soluble form of vitamin C. In this embodiment, the at least one oil insoluble form of vitamin C and the at least one oil soluble form of vitamin C can be added to the oil base together. Alternative, in this embodiment of the method, the at least one oil insoluble form of vitamin C can be added to the oil base before adding the at least one oil soluble form of vitamin C, or vice versa.

In the method of making the cosmetic composition of the present invention, the ingredients can be mixed in any order. In the method, (a) vitamin C and the at least one organic sulfur compound can be added to the oil base together, (b) vitamin C can added before the addition of the at least one organic sulfur compound, (c) vitamin C can be added after the addition of the at least one organic sulfur compound, (d) the at least one oil insoluble form of vitamin C can be added to the oil base, followed by the addition of the at least one organic sulfur compound, and then followed by the addition of the at least one oil soluble form of vitamin C, or (e) the at least one oil soluble form of vitamin C can be added to the oil base, followed by the addition of the at least one organic sulfur compound, and then followed by the addition of the at least one oil insoluble form of vitamin C.

A preferred form of the cosmetic composition of the present invention is a gel material whereby the at least one oil soluble vitamin C, e.g., ascorbyl palmitate, is dissolved in the oil base to form a gel and the gel has sufficient viscosity to retain particles of the at least one oil insoluble vitamin C in suspension so that they are evenly distributed during topical use. When using a gel form, it is preferred to first form the gel without the oil insoluble vitamin C. Once the gel is formed, the remaining non-vitamin C components can be added, followed by the final mixing in of the insoluble vitamin C crystals. The order of mixing can vary after gel formation, if desired.

In an embodiment of the method of making the cosmetic composition of the present invention, the ingredients are mixed using a special Cosmetic Mixer manufactured in Switzerland.

A preferred methodology first combines the ascorbyl palmitate with sunflower oil and grapeseed oil. This mixture is heated until the ascorbyl palmitate goes into solution. The heated solution is allowed to cool and is stirred while cooling. Putting the ascorbyl palmitate in solution and cooling forms a gel.

A next step combines the olive oil, cocoa butter and shea butter. This mixture is heated until melted and stirred into the gel.

Then, the jojoba oil, vitamin E, green tea extract, alpha lipoic acid, grapefruit extract and evening primrose oil are mixed together until smooth and added to the mixture of the gel and the olive oil, cocoa butter and shea butter.

Finally, oil insoluble vitamin C crystals are mixed to form the cosmetic composition. The composition can then be topically rubbed on an individual's skin for cleansing purposes as well as therapeutic purposes. In addition, the cosmetic composition could be used as a mask material to cover a given skin area for a select period of time. Other uses as would be known in the art also fall within the scope of the invention.

Other methodologies can be used to combine additives other than those disclosed above as part of the basic mix of insoluble vitamin C crystals and the oil base. The methodology described above is a preferred mode but other modes could also be used.

EXAMPLE 1

As an example, the present invention provides a cosmetic composition containing
calcium ascorbate, 19.5 weight %;
ascorbyl palmitate, 14.5 weight %;
methyl sulfonyl methane, 5 weight %;
sunflower oil, 14-16 weight %;
grapeseed oil, 14-16 weight %;
olive oil, 1-2 weight %;
shea butter, 18-22 weight %;
vitamin E, 1-2 weight %; and
cocoa butter, 4.5-6 weight %,
based on the weight of the cosmetic composition.

EXAMPLE 2

As another example, the present invention provides a cosmetic composition comprising
calcium ascorbate, 15 weight %;
ascorbyl palmitate, 19 weight %;

methyl sulfonyl methane, 10 weight %;
sunflower oil, 14-16 weight %;
grapeseed oil, 12-14 weight %;
olive oil, 1-2 weight %;
shea butter, 16-20 weight %;
vitamin E, 1-2 weight %; and
cocoa butter, 3.5-5 weight %, based on the weight of the cosmetic composition.

The present invention is not intended to be limited by the specific embodiments described above. Various changes, modifications and alterations from the teachings of the present invention may be contemplated by those skilled in the art without departing from the intended spirit and scope of the present invention.

What is claim is:

1. A cosmetic scrub composition, comprising
   19.5 weight % of calcium ascorbate,
   14.5 weight % of ascorbyl palmitate,
   5 weight % of methyl sulfonyl methane,
   14-16 weight % of sunflower oil,
   14-16 weight % of grapeseed oil,
   1-2 weight % of olive oil,
   18-22 weight % of shea butter,
   1-2 weight % of vitamin E, and
   4.5-6 weight % of cocoa butter,
based on the weight of the composition, wherein at least a portion of the calcium ascorbate exists as vitamin C particles in the composition suitable for use as a scrubbing agent, and wherein the sum of the amounts of calcium ascorbate, ascorbyl palmitate, methyl sulfonyl methane, sunflower oil, grapeseed oil, olive oil, shea butter, vitamin E and cocoa butter does not exceed 100 weight %.

2. A cosmetic scrub composition comprising an oil base, an effective amount of at least two forms of vitamin C, and at least one organic sulfur compound comprising methyl sulfonyl methane,
   wherein at least one of the two forms of vitamin C comprises at least one oil insoluble form of vitamin C and wherein at least a portion of the at least one oil insoluble form of vitamin C exists as vitamin C particles in the composition suitable for use as a scrubbing agent, and
   wherein the composition further comprises
   about 10 weight % to 20 weight % sunflower oil,
   about 12 weight % to 18 weight % grapeseed oil,
   about 1 weight % to 4 weight % olive oil,
   about 10 weight % to 30 weight % shea butter,
   about 1 weight % to 4 weight % vitamin E,
   about 2 weight % to 8 weight % cocoa butter,
   about 0.2 weight % to 1 weight % Jojoba oil,
   about 0.01 weight % to 0.06 weight % green tea extract,
   about 0.01 weight % to 0.06 weight % alpha lipoic acid,
   about 0.01 weight % to 0.06 weight % grapefruit extract, and
   about 0.2 weight % to 1.2 weight % evening primrose oil.

3. A cosmetic scrub composition, comprising
   15 weight % calcium ascorbate,
   19 weight % ascorbyl palmitate,
   10 weight % methyl sulfonyl methane,
   14-16 weight % sunflower oil,
   12-14 weight % grapeseed oil,
   1-2 weight % olive oil,
   16-20 weight % shea butter,
   1-2 weight % vitamin E and
   3.5-5 weight % cocoa butter,
based on the weight of the composition, wherein the sum of the amounts of calcium ascorbate, ascorbyl palmitate, methyl sulfonyl methane, sunflower oil, grapeseed oil, olive oil, shea butter, vitamin E and cocoa butter does not exceed 100 weight %, and wherein at least a portion of the calcium ascorbate exists as vitamin C particles in the composition suitable for use as a scrubbing agent.

* * * * *